United States Patent [19]

Plata et al.

[11] Patent Number: 5,342,981

[45] Date of Patent: Aug. 30, 1994

[54] SUBSTANTIALLY ISOMERICALLY PURE HEXANE OR HEXENE COMPOUNDS

[75] Inventors: Daniel J. Plata, Waukegan; Anthony K. L. Fung; Howard E. Morton, both of Gurnee; Robert Leanna, Mundelein; William R. Baker, Libertyville, all of Ill.; John K. Pratt, Kenosha, Wis.

[73] Assignee: Abbott Laboratories, Abbott Park, Ill.

[21] Appl. No.: 15,186

[22] Filed: Feb. 10, 1993

Related U.S. Application Data

[60] Division of Ser. No. 795,415, Nov. 20, 1991, Pat. No. 5,229,518, which is a continuation-in-part of Ser. No. 665,635, Mar. 6, 1991, abandoned.

[51] Int. Cl.$^5$ ............................................. C07F 7/02
[52] U.S. Cl. ............................. 556/420; 560/27; 560/29; 560/115; 564/355; 564/360; 564/454; 564/455
[58] Field of Search .................. 560/21, 23, 121, 123, 560/124, 29, 115, 27; 564/355, 455, 360, 454; 556/420

[56] References Cited

U.S. PATENT DOCUMENTS 4,880,781  11/1989  Hester et al. .......................... 514/18

FOREIGN PATENT DOCUMENTS 173481  3/1986  European Pat. Off. .
WO90/00166  1/1990  PCT Int'l Appl. .

OTHER PUBLICATIONS

Shiozaki, Tetrahedron Letters, vol. 30, No. 28, pp. 3669–3670, 1989.
Nishi, et al., Chemistry Letters, pp. 1993–1996, 1989.
Bradbury, et al. Tetrahedron Letters, vol. 30, No. 29, pp. 3845–3848, 1989.
Chakravarty, et al., Tetrahedron Letters, vol. 30, No. 4, pp. 415–418, 1989.
Holloday et al., Tetrahedron Lett., 1983, 24(41), 4401–4.
Thaisrivongs, J. Med. Chem, 1990, 33, 1337–1343.
Harbeson et al, J. Med. Chem., 1989, 32, 1378–1392.
Mikami et al, Tetrahedron Lett, 1990, 31(27), 3909–12.

*Primary Examiner*—C. Warren Ivy
*Assistant Examiner*—Zinna N. Davis
*Attorney, Agent, or Firm*—Steven R. Crowley

[57] ABSTRACT

The present invention relates to intermediates useful in a process for the preparation of a compound of the formula:

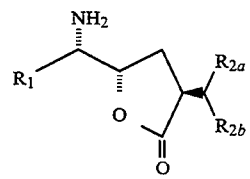

wherein $R_{2a}$ is hydrogen or loweralkyl, $R_{2b}$ is hydrogen, loweralkyl, cycloalkyl or phenyl and $R_1$ is cycloalkyl, cycloalkylalkyl, phenyl or benzyl. These intermediates are compounds of the formula:

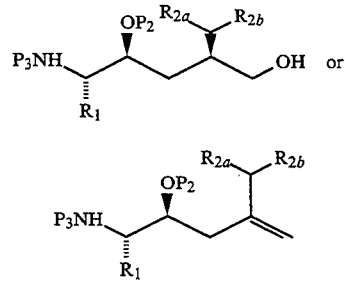

wherein $P_2$ is an O-protecting group, $P_3$ is an N-protecting group and $R_1$, $R_{2a}$ and $R_{2b}$ are defined as above.

8 Claims, No Drawings

SUBSTANTIALLY ISOMERICALLY PURE HEXANE OR HEXENE COMPOUNDS

This is a division of U.S. patent application Ser. No. 07/795,415, filed Nov. 20, 1991, now which is U.S. Pat. No. 5,229,518 a continuation-in-part of U.S. patent application Ser. No. 665,635, filed Mar. 6, 1991 now abandoned.

TECHNICAL FIELD

The present invention relates to a process and intermediates for the preparation of a hydroxyethylene dipeptide isostere.

BACKGROUND OF THE INVENTION

Hydroxyethylene dipeptide mimics are commonly employed as isosteric replacements for a dipeptide moiety in peptidyl enzyme inhibitors. For example, the substrate for renin contains a Leu-Val dipeptide moiety which is cleaved to produce angiotensin I, the precursor to the hypertensive peptide angiotensin II. A number of inhibitors of renin have been reported which incorporate a noncleavable mimic of the Leu-Val dipeptide having the formula 1.

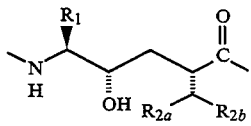

An intermediate that is commonly used to prepare compounds incorporating 1 ($R_1$ is loweralkyl, cycloalkyl, cycloalkylalkyl, phenyl or benzyl, $R_{2a}$ is hydrogen or loweralkyl and $R_{2b}$ is hydrogen, loweralkyl, cycloalkyl or phenyl) is the compound of formula 2. See Shiozaki, et al., Tet. Lett. 30 3669 (1989); Nishi, et al., Chem. Lett. 1993 (1989); Bradbury, et al., Tet. Lett. 30 3845 (1989); Chakravarty, et al., Tet. Lett. 30 415 (1989); Herold, et al., J. Org. Chem. 54 1178 (1989); Pals, et al., European Patent Application No. EP173481, published Mar. 5, 1986; and Wuts, PCT Patent Application No. WO90/00166, published Jan. 11, 1990.

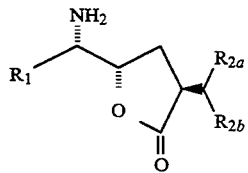

The reported syntheses of 2 are limited in their ability to readily provide stereochemically pure products with a minimum amount of purifications and isomeric separations. Thus, there is a continuing need to develop more effective syntheses of 2 ($R_1$ is loweralkyl, cycloalkyl, cycloalkylalkyl, phenyl or benzyl, $R_{2a}$ is hydrogen or loweralkyl and $R_{2b}$ is hydrogen, loweralkyl, cycloalkyl or phenyl).

DISCLOSURE OF THE INVENTION

The present invention relates to a process for the preparation of a substantially isomerically pure compound (>95% isomerically pure) of the formula 2 ($R_1$ is loweralkyl, cycloalkyl, cycloalkylalkyl, phenyl or benzyl, $R_{2a}$ is hydrogen or loweralkyl and $R_{2b}$ is hydrogen, loweralkyl, cycloalkyl or phenyl). A process for the preparation of 2 is shown in Scheme 1. An L-amino acid or L-amino acid derivative 3 ($R_1$ is loweralkyl, cycloalkyl, cycloalkylalkyl, phenyl or benzyl) is esterified ($R_3$ is loweralkyl or benzyl) and the amino group is protected with an N-protecting group that protects the amino group during subsequent reactions and also protects during subsequent reactions against racemization of the chiral carbon to which the amino group is bonded to provide 4. N-protecting groups $P_1$ include, but are not limited to, triphenylmethyl, triphenylmethyl wherein one or more of the phenyl rings is substituted with a loweralkyl, halo or alkoxy group (for example, (p-methoxyphenyl)diphenylmethyl, diphenyl-4-pyridylmethyl, 9-phenylfluoren-9-yl or 5-dibenzosuberyl and the like). Compound 4 is converted to β-ketophosphonate 5 ($R_4$ is loweralkyl) by reaction with the anion of a methylphosphonate ester. The anion is prepared by treating the methylphosphonate ester with a base (for example, n-BuLi or other loweralkyllithium) at low temperature (for example, −78° C. to −60° C.) in an inert solvent such as tetrahydrofuran (THF), dimethoxyethane (DME), dioxane and the like. Reaction of the enolate of 5 (prepared by treatment with a base (for example, NaH, KH, lithium diisopropylamide, lithium tetramethylpiperidide and the like) at low temperature (for example, 0° C.→ambient temperature) in an inert solvent such as THF, DME, dioxane and the like) with the sodium or other salt of ($R_{2a}$) ($R_{2b}$)CHC(O)CO$_2$H ($R_{2a}$ is hydrogen or loweralkyl, $R_{2b}$ is hydrogen, loweralkyl, cycloalkyl or phenyl) provides 7. Alternatively, treatment of the enolate of 5 with ($R_{2a}$)($R_{2b}$)CHC(O)CO$_2$R$_5$ ($R_5$ is loweralkyl) provides the olefinic ester 6. Saponification with a mild base (for example, LiOH/MeOH/H$_2$O/THF), accompanied by olefin isomerization, provides 7.

Formation of an activated ester derivative of acid 7 provides 8 ($R_6$ is an activating group for amide bond formation, for example, N-succinimidyl, N-benzotriazolyl, N-5-norbornene-2,3-dicarboximide, isobutyloxycarbonyl, 2,4,5-trichlorophenyl, p-nitrophenyl, 2, 4-dinitrophenyl and the like). Removal of the N-protecting group $P_1$ (for example, by treatment with acid or hydrogenolysis) and neutralization with a base (such as imidazole, NaHCO$_3$ and the like) results in cyclization to keto-lactam 9. Reduction of 9 (for example, with L-Selectride ® at low temperature (−78° C. to 0° C.) in an inert solvent (such as CH$_2$Cl$_2$, THF and the like) ) provides 10. Alternatively, 9 can be prepared by deprotection of 7, followed by lactam formation in the presence of an amide coupling reagent (such as ethyl dimethylaminopropyl carbodiimide/4-methyl morpholine, dicyclohexylcarbodiimide, bis(2-oxo-3-oxazolidinyl)phosphinic chloride and the like). Hydrogenation of olefin 10 (for example, with H$_2$ Pd/C) provides saturated lactam 11. Isomerization of 11 under acidic conditions (for example, 6N HCl in ethanol or other acids in alcoholic solvents) provides 2.

In a preferred embodiment of this invention, L-phenylalanine is converted to N-triphenylmethyl cyclohexylalanine methyl ester 12 (Scheme 2). Ester 12 is treated with the lithium anion of dimethyl methylphosphonate to provide β-ketoester 13. Treatment of the sodium enolate of 13 with methyl-3-methyl-2-oxobutanoate provides olefinic ester 14. Mild basic saponification of 14, accompanied by olefin isomerization, gives 15.

Acid 15 is converted to the N-hydroxsuccinimide activated ester 16. Acidic deprotection, followed by neutralization with base, provides keto-lactam 17. Crude 17 is reduced with L-Selectride® at reduced temperature (−78° C.) to give exclusively the axial alcohol 18. Hydrogenation of 18 provides 19 as a single diastereomer. Treatment of 19 in 6N HCl provides the lactone 20.

A process for the preparation of 2b, N-protected compound 2, is shown in Scheme 3. L-amino acid derivative 22 is obtained by reacting 21 with methylchloroformate, triethylamine and an appropriate substituted amine as described below. (N-protecting groups $P_3$ include, but are not limited to, t-butoxycarbonyl, benzyloxycarbonyl and the like. $R_1$ is loweralkyl, cycloalkyl, cycloalkylalkyl, phenyl or benzyl and $R_7$ is, for example, 3,5-dimethylpyrazolyl, pyrrolidinyl, tetrahydroisoxazolyl, methoxybenzylamino or methoxymethylamino and the like). 22 is reduced to a protected amino aldehyde 23 (for example, by metal hydride reduction (lithium aluminum hydride or sodium bis (2-methoxyethoxy) aluminum hydride and the like)). Alternatively, aldehyde 23 is prepared from acid 21 or ester 22 ($R_7$ is alkoxy) by diborane or metal hydride reduction to the primary alcohol and oxidation of the alcohol to the aldehyde by a variety of oxidative methods (for example, Swern oxidation, sulfur trioxide/pyridine, NaOCl/TEMPO and the like). Reaction of aldehyde 23 with a 2-substituted allylsilane ($CH_2=C(CH(R_{2a})(R_{2b}))$ ($CH_2SiR_{2c}R_{2d}R_{2e}$)) at low temperature (−70° C. to 0° C.) in an inert anhydrous solvent (for example, dichloromethane, dichloroethane, THF and the like) in the presence of a catalyst (for example, titanium tetrachloride, tin tetrachloride or boron trifluoride and the like) provides the homoallylic alcohol 24. ($R_{2a}$ is hydrogen or loweralkyl, $R_{2b}$ is hydrogen, loweralkyl, cycloalkyl or phenyl and $R_{2c}$, $R_{2d}$ and $R_{2e}$ are independently selected from loweralkyl and phenyl). Alcohol 24 is protected as an ether or ester 25. Examples of ether and ester protecting groups ($P_2$) include, but are not limited to, trimethylsilyl, tert-butyldimethylsilyl and tert-butyldiphenylsilyl, dihydropyranyl, acetyl, benzoyl and the like.

Hydroboration (for example, using diborane, an alkylborane or a dialkylborane and the like) of 25 in an inert solvent (for example, THF, diethyl ether or dimethoxymethane and the like) affords the primary alcohol 26. When $P_2=H$, oxidation (for example, $RuO_4$, Jones reagent, Pt metal/oxygen and the like) of 26 produces the lactone 2b directly. When 26 is protected (for example $P_2$ =tert-butyldimethylsilyl (TBDMS), tert-butyldiphenylsilyl and the like), oxidation (for example, $RuO_4$, Jones reagent, Pt metal/oxygen and the like) produces a carboxylic acid intermediate 27 which upon acidification (for example, methanolic HCl, boron trifluoride etherate in methylene chloride or p-toluenesulfonic acid in benzene and the like) cleaves the hydroxyl protecting group and cyclizes the hydroxy acid to give the protected lactone 2b.

In cases where lactone 2b is contaminated with undesired C(2) β-diastereomer 2c, the lactone enolate 28a is formed by treating the mixture of lactones with a strong base (for example, LDA, LiN (TMS)$_2$ and the like) in a nonpolar solvent (for example, diethyl ether, hexane or mixtures of both) at low temperature (for example, −100° C. to −78° C.). The lactone enolate 28a can be trapped with trimethylsilylchloride to give the enol silyl ether 28b. Enolate 28a can be regenerated from 28b free of secondary amine by reaction with methyllithium in diethyl ether. Optically active (R or S) α-hydroxy esters (where $R_9$ and $R_{10}$ are independently selected from loweralkyl, aryl and arylalkyl and $R_{11}$ is loweralkyl) (for example, ethyl lactate, ethyl phenyllactate, ethyl mandelate, ethyl 2-hydroxyhexanoate and the like) or (+) or (−)-diethyl tartarates, (R) or (S) diethyl malate or 2-substituted diethyl malonates (R is loweralkyl, phenyl, p-nitrophenyl, nitro, halogen, cyano, phenylsulfonyl or diethylphosphonyl and the like), reagents for the stereoselective kinetic protonation of the enolate, are added to the enolate at low temperature (for example, −100° C. to −78° C.). Warming to room temperature affords the protected lactone 2b enriched in either the α- or β-diastereomer depending on the proton source.

In a preferred embodiment of this invention, L-cyclohexylalanine is converted to N-CBz-cyclohexylalanine N-methyl-N-methoxycarboxamide 29 (Scheme 4). Reaction of the amide with lithium aluminum hydride in diethyl ether affords aldehyde 30 which can be used in the next step without further purification. Treatment of 30 with silane 35 in dichloromethane at −78° C. followed by 2 equivalents of stannic chloride gives the homoallylic alcohol 31 and its C(3) epimer in a ratio of 10: 1. These isomers can be separated by chromatography. Hydroboration of 31 ($P_2$=TBDMS) with diborane in THF at 0° C. gives a 2. 5: 1 mixture of diol diastereomers 32 and C(5) epi-32 which can be separated by chromatography. The lactone 33 is obtained from pure diol 32 by ruthenium tetroxide oxidation and cyclization with hydrochloric acid in methanol. Alternatively, the 2.5:1 mixture of alcohols 32 and C(5) epi-32 can be oxidized using ruthenium tetroxide and cyclized with hydrochloric acid in methanol to give a 88:12 mixture of lactones 33 and C(2) epi-33 after recrystallization. Further elaboration of the lactone mixture either as the free amine or N-Cbz- or N-Boc-protected amine with an amine (for example, 3-(4-morpholinyl)propylamine) (10 equivalents) and acetic acid (3 equivalents) at 60 ° C. for several hours gives the hydroxyethylene isostere.

(2-Isopropyl-2-propenyl)trimethyl silane 35 is prepared by reacting the enol phosphonate of isopropyl methyl ketone 34 with trimethylsilylmethylmagnesium chloride and nickel acetylacetonide. Alternatively, silane 35 is prepared by metalation of 2-isopropyl-2-propene 37 with sec-butyllithium/TMEDA and trapping the anion with chlorotrimethylsilane. Silane 35 is also prepared by reaction of methyl isobutyrate 36 with trimethylsilylmethyl-cerium dichloride according to the procedure of Bunnelle and Narayanan, Org. Syn. 69, 89–95 (1990).

Alternatively, 32b, the diastereomeric mixture from the hydroboration of 31 (nitrogen-protected with Cbz and alcohol-protected as the t-butyldimethylsilyl ether), is oxidized using ruthenium tetroxide and sodium periodate to give carboxylic acid 38 (Scheme 5). Cyclization of 38 (using for example, DCC/DMAP or oxalyl chloride, DMF, DMAP and triethylamine and the like) gives lactam 39. Equilibration of 39 using 1,8-diazabicyclo[5.4.0]undec-7-ene (DBU) in acetonitrile affords the C(2) -α-diastereomer 40. Lactam 40 can be converted to lactone 33 using hydrochloric acid in methanol. Lactone 33 can be reacted with an amine (for example, 3-amino-1-(morpholin-4-yl)propane) to give 41. Alternatively, lactam 40 can be reacted directly with an amine, with or without acetic acid as a catalyst, to give 41.

Yet another alternative synthesis of lactone 2b is illustrated in Scheme 6. The dianion of the prolinolamide 43 ($R_{2a}$ is hydrogen or loweralkyl, $R_{2b}$ is hydrogen, loweralkyl, cycloalkyl or phenyl) in an inert solvent (for example, THF, diethyl ether or dimethoxyethane and the like) at a temperature of from about −78° C. to about −25° C. is reacted with the lithio epoxide 42 ($P_3$ is an N-protecting group and $R_1$ is loweralkyl, cycloalkyl, cycloalkylalkyl or benzyl) to produce the hydroxy lactone 44. Epoxide 42 is prepared from aldehyde 23 (Scheme 3) via the known Boc epoxide (Luly et al., J. Med. Chem. 31, 532–39 (1988)) by reaction with n-butyllithium. Cyclization of 44 under acidic conditions (for example, methanolic HCl or boron trifluoride etherate in methylene chloride and the like) affords lactone 2b ($P_3$=Boc or CBz).

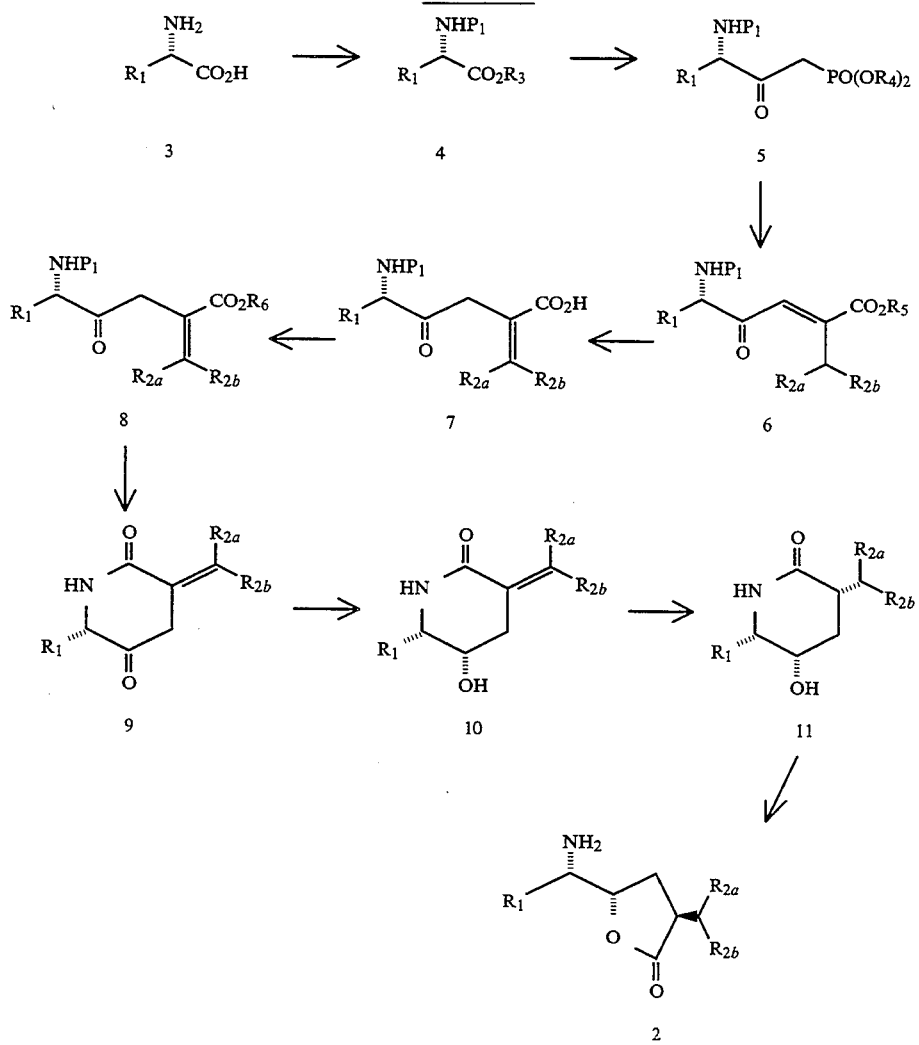

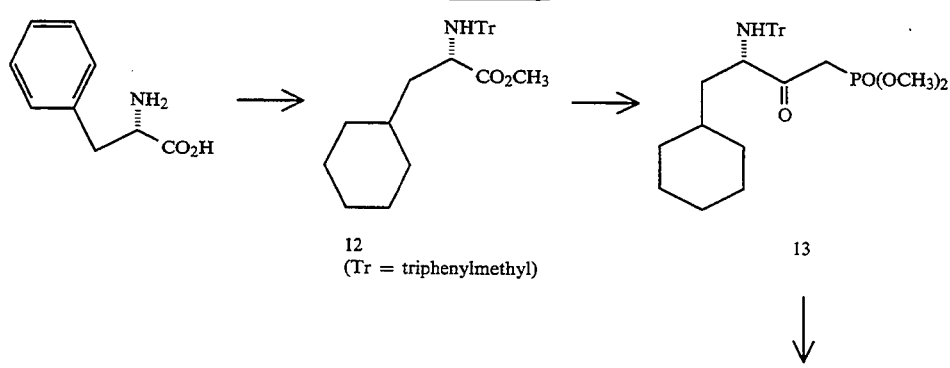

SCHEME 2
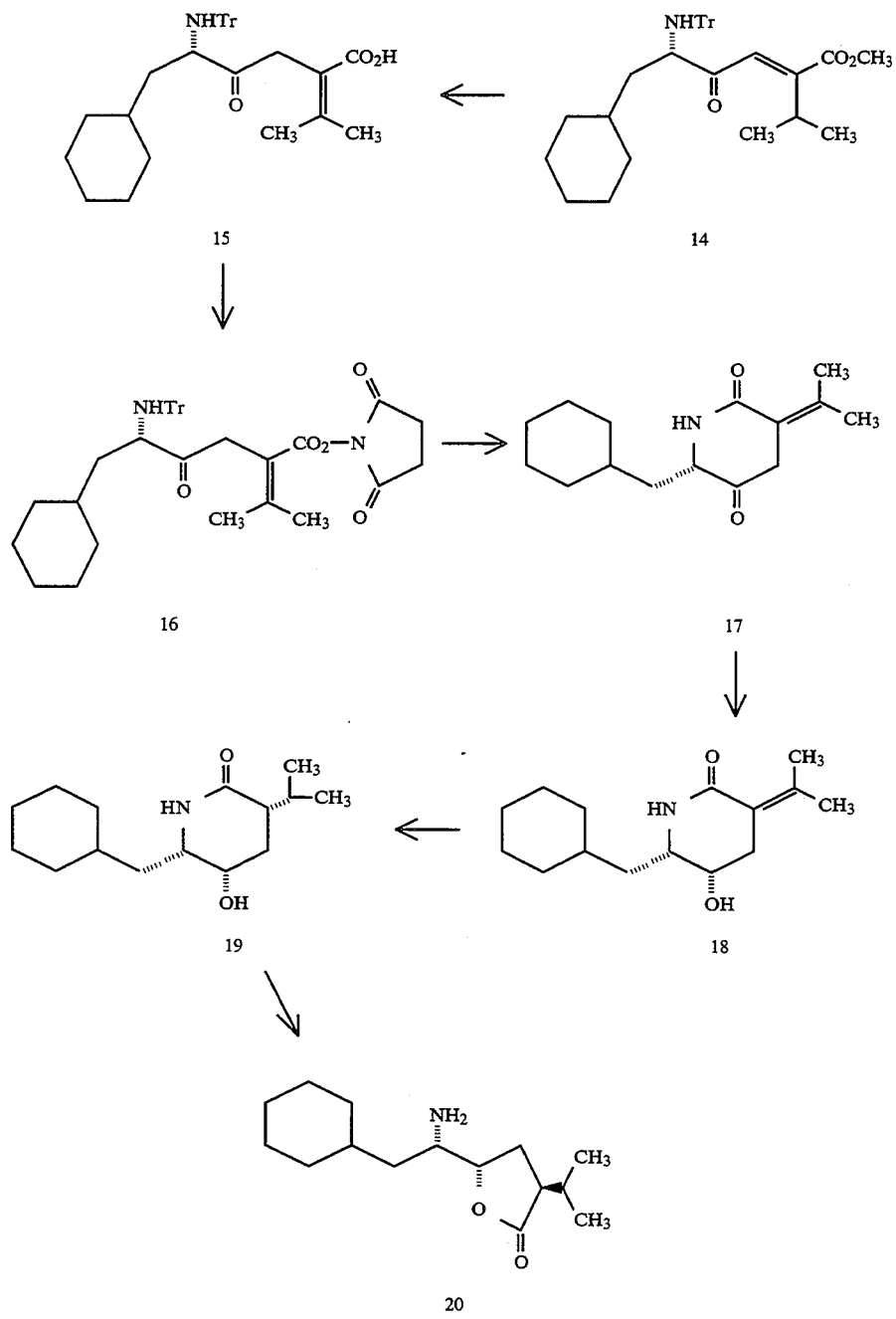
SCHEME 3
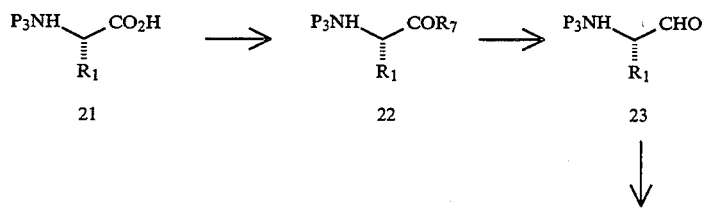

-continued
SCHEME 3
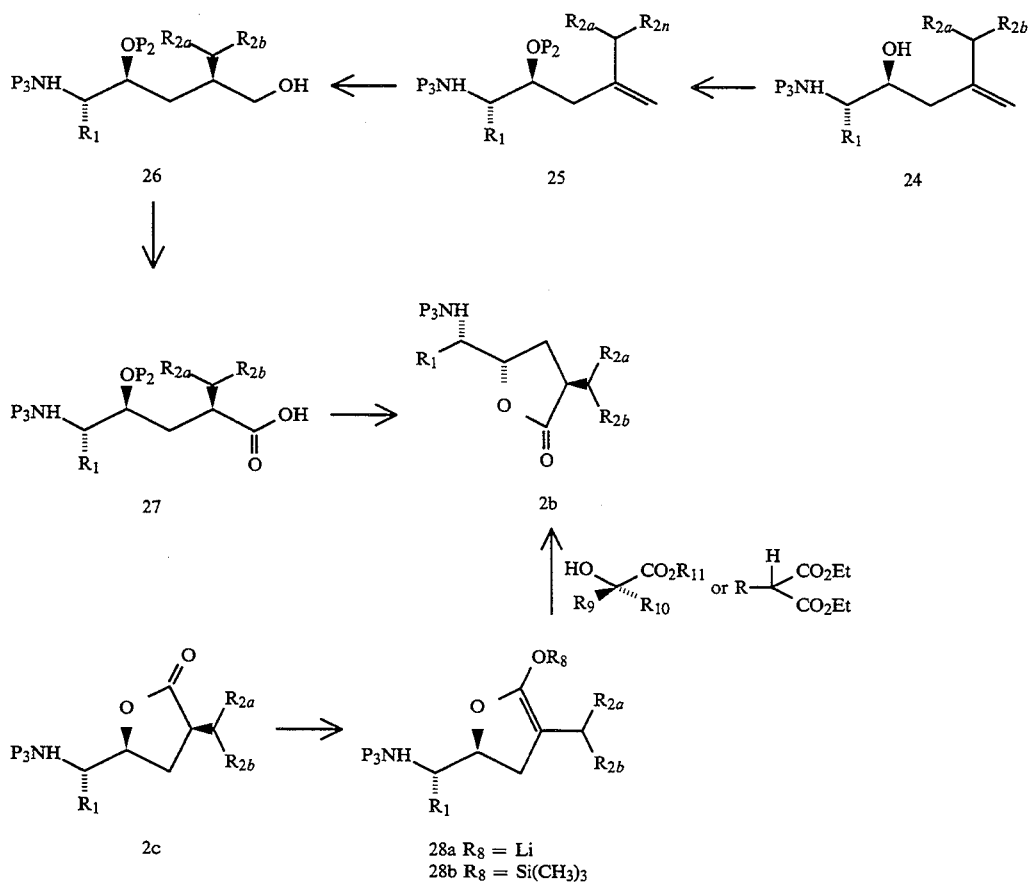
SCHEME 4
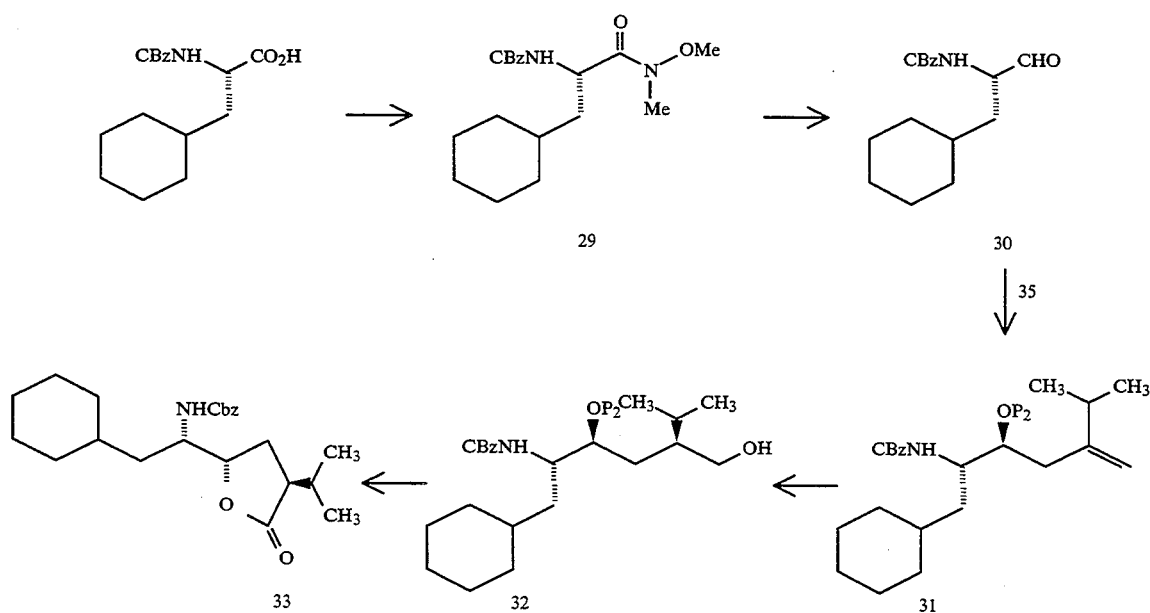

-continued
SCHEME 4
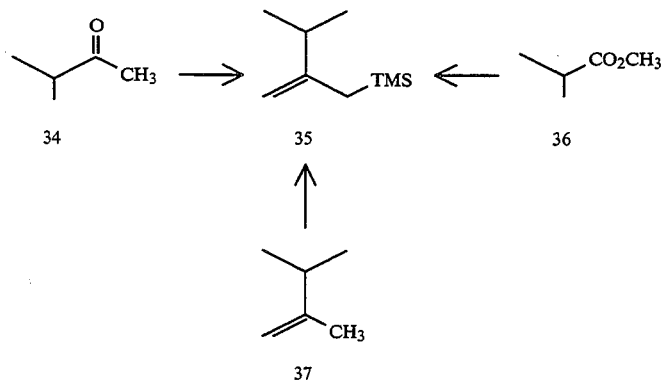
SCHEME 5
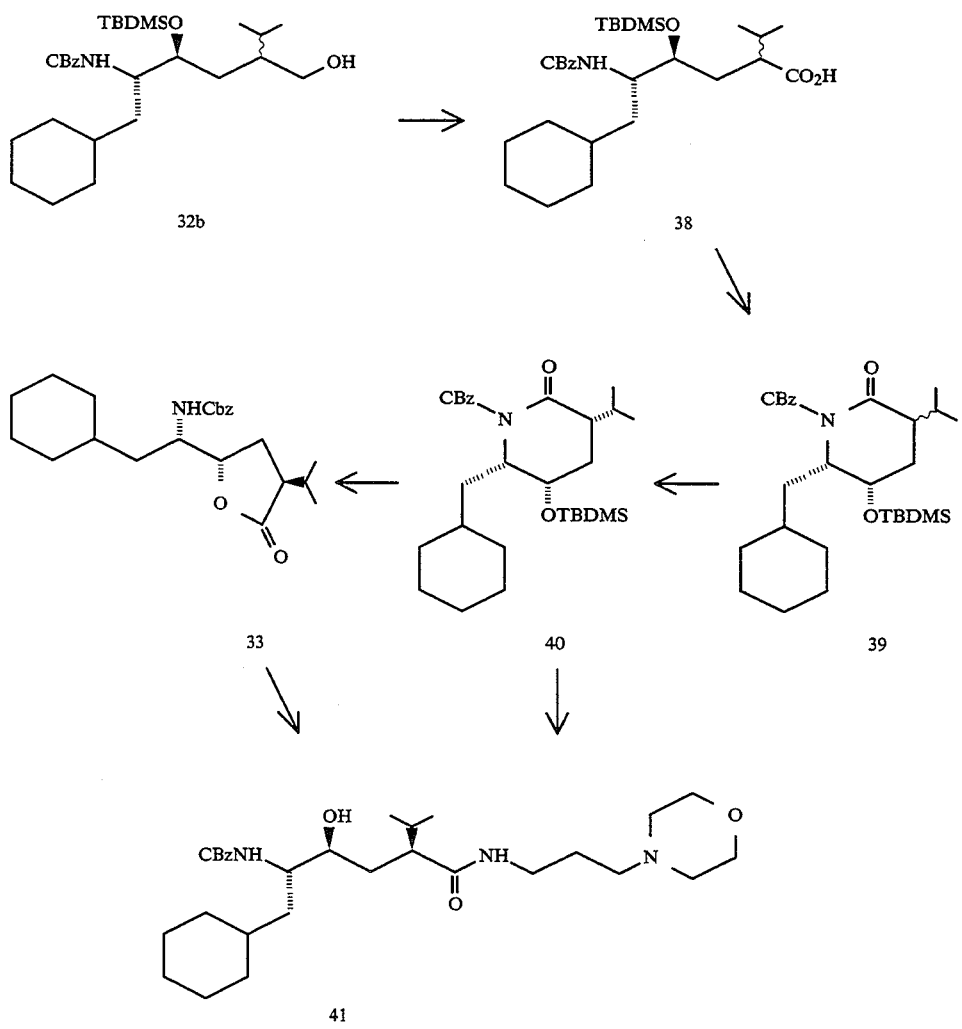

SCHEME 6

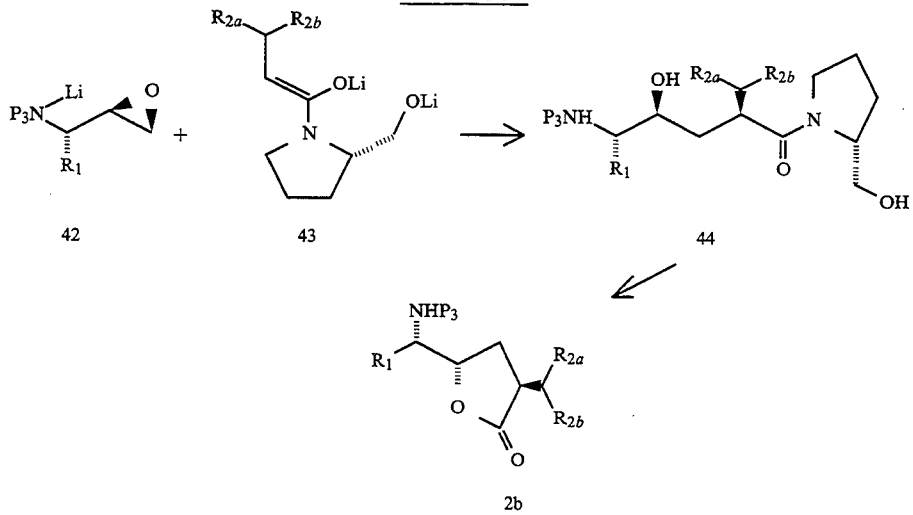

The term "loweralkyl" as used herein refers to straight or branched chain alkyl radicals containing from 1 to 7 carbon atoms including but not limited to methyl, ethyl, n-propyl, iso-propyl, n-butyl, iso-butyl, sec-butyl, n-pentyl, 2-methylbutyl, 2,2-dimethylpropyl, n-hexyl, 2-methylpentyl, 2,2-dimethylbutyl, n-heptyl, and the like.

The term "cycloalkyl" as used herein refers to an alicyclic ring having 3 to 7 carbon atoms.

The term "cycloalkylalkyl" as used herein refers to a cycloalkyl residue appended to a loweralkyl radical and includes, but is not limited to, cyclohexylmethyl and cyclopentylmethyl.

The term "halo" as used herein refers to Cl, Br, F or I substituents.

The term "alkoxy" as used herein refers to $R_{10}O$- wherein $R_{10}$ is a loweralkyl group.

The term "hydroxy-protecting group" or "O-protecting group" as used herein, refers to a substituent which protects hydroxyl groups against undesirable reactions during synthetic procedures and includes, but is not limited to, substituted methyl ethers, for example, methoxymethyl, benzyloxymethyl, 2-methoxyethoxymethyl, 2-(trimethylsilyl) ethoxymethyl, benzyl, and triphenylmethyl; terahydropyranyl ethers and substituted ethyl ethers, for example, 2,2,2-trichloroethyl and t-butyl; silyl ethers, for example, trimethylsilyl, t-butyldimethylsilyl and t-butyldiphenylsilyl.

The following examples will serve to further illustrate the process of the invention.

EXAMPLE 1

(2S)-Cyclohexylalanine methyl ester, hydrochloride salt

L-Phenylalanine (215 g, 1.3 tool) was hydrogenated over Pd/C in HOAc, filtered and concentrated. The resulting cyclohexylalanine was taken up in MeOH (1200 mL). Thionyl chloride (427 g, 3.59 mole) was slowly added to the slurry, which eventually became homogeneous. The reaction was cooled in an ice/water bath and addition of thionyl chloride was continued. The reaction mixture was heated to reflux for 2 hours, cooled and concentrated to afford a solid, which was taken up in ether and filtered. The white solid was washed with ether in the filter funnel and dried in vacuo to give 271 g of the title product, 94% yield over two steps. m.p. 150°-152° C. $[\alpha]_D = +21.8°$ (c=1.09, MeOH). IR (KBr) 2930 (br), 2860, 1748 cm$^{-1}$. $^1$H NMR (300 MHz, CDCl$_3$) δ3.99 (t, J=6.3 Hz, 1H), 3.9 (bs, 2H), 3.83 (s, 3H), 1.82-1.65 (m, 7H), 1.5 (m, 1H), 1.35-1.10 (m, 3H) 1.05-0.9 (m, 2H); $^{13}$C NMR (75.5 Hz, CDCl$_3$) ppm 170.5, 53.3, 50.8, 38.3, 33.6, 33.0, 32.8, 26.3, 26.1, 25.9.

EXAMPLE 2

(2S)-N-(Triphenylmethyl)cyclohexylalanine methyl ester

The product of Example 1 (88 g, 398 retool) was taken up in chloroform (400 mL). Triethylamine (84.6 g, 836 retool) was then added in one portion to the slurry and stirred five minutes. Triphenylmethylchloride (111 g, 398 mmol) was then added, and the reaction was stirred for 5 hours at ambient temperature. The internal temperature of the reaction reached 50° C., however, external cooling was not employed. The reaction mixture was washed with 1M KHSO$_4$ solution (2×200 mL), saturated NaHCO$_3$ (200 mL), brine (100 mL), then dried over MgSO$_4$. The solution was then concentrated to give 200 g of residue which was filtered through 900-1000 g of silica gel (elution gradient hexane-10:1 hexane: ethyl acetate) affording 157 g of product (93%), which could be crystallized from hexanes: ethyl acetate to afford large white crystals. m.p. 86°-87° C. $[\alpha]_D = +73.6°$ (c=1.38, CHCl$_3$). IR (KBr), 3450(br), 2930, 1722 cm$^{-1}$. $^1$H NMR (300 MHz, CDCl$_3$) δ7.52-7.47 (m, 6H), 7.28-7.12 (m, 9H), 3.32-3.41 (m, 1H), 3.12 (s, 3H), 2.60 (d, J=10.5 Hz, 1H), 1.56-1.46 (m, 7H), 1.35-1.1 (m, 4H), 0.77-0.97 (m, 2H). $^{13}$C NMR (75.5 Hz, CDCl$_3$) ppm 176.1, 146.0, 128.8, 127.7, 126.3, 71.0, 54.2, 51.2, 44.4, 34.1, 33.9, 32.9, 26.5, 26.1.

EXAMPLE 3

Dimethyl (3S)-4-Cyclohexyl-3-(N-triphenylmethyl) amino-2-oxobutylphosphonate

To a −78° C. solution of dimethyl methylphosphonate (272.5 g, 2.2 tool) in 1.6 L THF was added n-BuLi (2.5 M, 800 mL, 2.0 mmol) and stirred 45 minutes. The product of Example 2 (156 g, 366 retool) in 40 mL THF was then added dropwise. The reaction mixture was stirred at −50° C. for 3 hours, then at −40° C. for 6 hours, then finally warmed to ambient temperature overnight. The reaction mixture was concentrated, taken up in ether, washed with 1M KHSO$_4$, saturated NaHCO$_3$ (twice) and brine, dried and concentrated. The residue (200 g) was filtered through 1000 g silica gel, (1:1 hexanes:ethyl acetate) to give 135 g of β-keto phosphonate (72%) as an oil. [α]$_D$=+39.7° (C =2.0, CH$_3$OH). IR (CDCl$_3$) 2920, 1717, 1425, 1226, 1019 cm$^{-1}$. $^1$H NMR (300 MHz, CDCl$_3$) δ7.45–7.38 (m, 6H), 7.30–7.18 (m, 9H), 3.67 (dd, J=11.1, 2.7 Hz, 6H), 3.47 (m, 1H), 2.83 (d, J=6.6 Hz, 1H), 2.67 (dd, J=21.0, 15.3 Hz, 1H), 2.32 (dd, J=21.0, 15.3 Hz, 1H), 1.65 (bs, 5H), 1.49 (m, 2H), 1.10-1-53 (m, 4H), 0.81 (m, 2H). $^{13}$C NMR (75.5 Hz, CDCl$_3$) ppm 205.8, 145.9, 129.1, 127.9, 127.7, 126.7, 71.2, 61.4, 61.3, 52.8, 52.7, 52.6, 41.4, 37.1, 35.2, 33.8, 33.5, 33.4, 26.4, 26.2, 26.1.

EXAMPLE 4

(6S) -7 -Cyclohexyl-2 -methyl-6-(N-triphenylmethyl)-amino-5-oxohept-2-ene-3-oic acid The product of Example 3 (117.2 g, 229 retool) was dissolved in 600 mL THF and cooled to 0° C. To this solution was added hexanes-washed NaH (60%, 9.6 g (wet), 240 mmol) and stirred 30 minutes. Next was added methyl 3-methyl-2-oxobutyrate (29.8 g, 229 retool) in 100 mL THF and stirred at 0° C. for 4 hours. Volatiles were removed at reduced pressure, the residue was dissolved in 1:1 hexanes:ether (500 mL) and washed with water (200 mL), NaHCO$_3$ (200 mL), brine (200 mL), dried (MgSO$_4$) and concentrated to afford 129 g of the desired ester as an oil.

This material (123 g) was taken up in 460 mL THF, 229 mL MeOH, cooled to 0° C., then 18.86 g of LiOH-H$_2$O in 229 mL of distilled water was added. This solution was allowed to warm to ambient temperature and stirred for 3 days. Volatiles were removed at reduced pressure and the resulting aqueous solution was washed with ether (100 mL×2) then acidified to pH 3 with 6N HCl. The aqueous solution was then extracted with EtOAc (2×300 mL), washed with brine, dried (MgSO$_4$) and concentrated to give 116 g of a yellow foam. This material was recrystallized from 525 mL of hot hexanes/EtOAc (12:1) to give 72.4 g of a white solid (62% for three steps). m.p. 97°–98° C. [α]$_D$=+6.0° (c=1.0, CH$_3$OH). IR (KBr) 3450(br), 2930, 1715, 1682, 1442 cm$^{-1}$. $^1$H NMR (300 MHz, CDCl$_3$) δ7.48–7.36 (m, 6H), 7.31–7.12 (m, 9H), 3.5 (bs, 1H), 3.25 (d, J=18 Hz, 1H), 2.99 (d, J=18H, 1H), 2.1 (bs, 4H), 1.6 (bs, 8H), 1.2–1.05 (m, 6H), 0.8–0.6 (m, 2H).

EXAMPLE 5

(5S, 6S) -6-Cyclohexylmethyl-3-isopropylidene-5-hydroxypiperidine-2-one

A solution of 3.06 g (6.0 mmol) of the product of Example 4 in 50 mL THF was added to 6.8 g (60 mmol) N-hydroxysuccinimide This homogeneous solution was cooled to 0° C., then dicyclohexylcarbodiimide (DCC) (1.25 g, 12 mmol) in 5 mL THF was added. The cooling bath was removed and the reaction was stirred for 2 hours. Then an additional 1.25 g of DCC was added. After 5 hours of total reaction time, the mixture was filtered, concentrated and dissolved in ether. The organics were washed with NaHCO$_3$ solution (2×50 mL) and brine, dried (MgSO$_4$) and concentrated at reduced pressure to give 5.2 g of product as an oil, which was dissolved in 20 mL ether. A 1N solution of HCl/ether (30 mL) was added. A gummy solid immediately precipitated out of solution; methylene chloride (25 mL) was added and the clear reaction mixture was stirred overnight. After 12 hours, the product, which precipitated from the mixture, was collected by filtration and washed with ether to give, after drying, 2.1 g of a white solid in 87% for two steps, which was taken on in the following step.

To a 0° C. slurry of this white solid (1.2 g, 3.0 retool) in 20 mL of methylene chloride was added imidazole (204 rag, 3.0 retool). The resulting reaction mixture was stirred for 1 hour, then washed with 20 mL of KHSO$_4$, water, saturated NaHCO$_3$, and brine. The organic portion was dried over MgSO$_4$, filtered and cooled to −78° C. To the cold solution was added L-Selectride® (Aldrich, 1.0 M, 5.0 mL, 5.0 mmol) and stirred for 10 minutes. The reaction mixture was then warmed to −40° C. and quenched with 20% citric acid solution. The organics were washed with 20 mL of water, saturated NaHCO$_3$ solution and brine, dried over MgSO$_4$, and concentrated to afford a clear oil. The oil was purified on silica gel eluting with 50% hexanes/ethyl acetate to give an oil which was triturated with ether to afford a white solid (545 rag, 72%). m.p. 128°–130° C. [α]$_D$=−66.3° (c=1.0, CH$_3$OH). IR (KBr) 3350(br), 2930, 1640, 1603 cm$^{-1}$. $^1$H NMR (300 MHz, CDCl$_3$) δ5.82 (bs, 1H), 3.95 (bs, 1H), 3.42 (m, 1H), 2.88 (bs, 1H), 2.72 (m, 1H), 2.55 (m, 1H), 2.25 (s, 3H), 1.8 (s, 3H), 1.77–1.6 (m, 5H), 1.52–1.34 (m, 3H), 1.28–1.12 (m, 3H), 1.0–0.83 (m, 2H). $^{13}$C NMR (75.5 Hz, CDCl$_3$) ppm 168.1, 148.0, 119.4, 66.3, 53.1, 38.4, 35.3, 33.7, 33.6, 32.9, 26.4, 26.1, 26.0, 23.2, 23.0.

EXAMPLE 6

(3S: 5S, 6S) -6-Cyclohexylmethyl-5-hydroxy-3-isopropylpiperidin-2-one

A solution of the product of Example 5 (24.7 g, 98.4 retool) in 500 mL of ethyl acetate was treated with 2.5 g of dry palladium on carbon and hydrogenated at 4 atmospheres of hydrogen for 4 hours at ambient temperature. The reaction mixture was filtered and concentrated to a white foamy solid which was taken on without further purification. m.p. 97°–99° C. [α]$_D$=−95.1° (c=1.075, CHCl$_3$). IR (KBr) 3605, 3400, 2925, 1642 cm$^{-1}$. $^1$H NMR (300 MHz, CDCl$_3$) δ6.3 (bs, 1H), 4.11 (m, J=4.5, 1H), 3.47 (m, 1H), 2.72 (bs, 1H), 2.5 (m, 1H), 2.3 (m, 1H), 1.9 (m, 1H), 1.8–1.5 (m, 8H), 1.43–1.12 (m, 6H), 0.97 (d, 3H), 0.87 (m, 3H). $^{13}$C NMR (75.5 Hz, CDCl$_3$) ppm 174.2, 67.1, 52.6, 44.3, 37.7, 34.5, 33.8, 32.4, 27.6, 26.4, 26.3, 26.2, 26.0, 20.2, 17.4.

EXAMPLE 7

(2S, 4S, 5S)-5-Amino-6-cyclohexyl-2-isopropyl-4-hexanolide

The product of Example 6 was dissolved in 200 mL of 6N HCl and 50 mL of ethanol then heated to reflux for 14 hours. The react ion mixture was concentrated at reduced pressure and azeotroped with toluene to afford a pale oil. This material was dissolved in water and washed with hexane; the aqueous phase was made basic by the addition of a solution of NaHCO$_3$. Extraction with ethyl acetate, followed by drying (MgSO$_4$) and removal of volatiles under reduced pressure afforded a yellowish oil which solidified to a white solid upon standing. Recrystallization from hexane gave 20.7 g (90%) of product as white needles. m.p. 49°–50° C. (lit. m.p. 48°–49° C.). IR (KBr) 2925, 1760 cm$^{-1}$. $^1$H NMR (300 MHz, CDCl$_3$) δ4.2 (q, J=6.1 Hz, 1H), 282 (q, J=6.2 Hz, 1H), 2.64 (ddd, J=9.1, 6.0, 5.4 Hz, 1H), 2.15 (m, 1H), 2.08 (m, 2H), 1.8–1.61 (m, 6H), 1.46 (m, 1H), 1.37–1.13 (m, 8H), 1.02 (d, J=6.0 Hz, 3H), 0.96 (d, J=6.0 Hz, 3H). $^{13}$C NMR (75.5 Hz, CDCl$_3$) ppm 178.9, 83.1, 52.6, 46.0, 41.3, 34.4, 33.7, 32.3, 29.2, 26.8, 26.5, 26.3, 26.0, 20.3, 18.5. [α]$_D$=+6.5° (c=1.0, EtOH).

EXAMPLE 8

3-(4-Morpholinyl)propyl (2S,4S,5S)-5-Benzyloxycarbonylamino-6-cyclohexyl-4-hydroxy-2-isopropylhexanamide To a solution of the product of Example 7 (20.7 g, 81.8 mmoles) in 100 mL of dimethylformamide (DMF) was added N-(benyloxycarbonyloxyl) succinimide ( 24.5 g, 92.8 mmoles) and triethylamine (11.4 mL, 81.1 mmol). This solution became warm, but external cooling was not applied. The reaction mixture was stirred overnight (14 hours) at ambient temperature and then poured into 250 mL of water, which resulted in precipitate formation. The white precipitate was filtered, washed with water and dried under vacuum at 40° C. to give a white powder in quantitative yield. This material could be recrystallized from ethyl acetate/hexane to give the N-Cbz protected amino lactone.

3-Amino-1- (morpholin-4-yl) propane ( 100 g, 693 retool) and the N-Cbz protected amino lactone from above (30.0 g, 77.5 mmoles) were combined, and to this slurry was added acetic acid (4.4 mL, 77.5 mmoles). This reaction mixture was heated to 70° C. and stirred 18 hours. The clear reaction mixture was cooled to ambient temperature, poured into 500 mL of ethyl acetate and washed with saturated NaHCO$_3$, water and brine. The organic layer was dried (MgSO$_4$) and concentrated to give a white solid which was taken up in 100 mL of ethyl acetate and stored overnight in the freezer. Filtration of the precipitated product, followed by drying, afforded 29.7 g of the desired product, which is useful for the preparation of renin inhibitors (see PCT Patent Application No. WO90/03971, published Apr. 19, 1990).

EXAMPLE 9

(3S,5S,6S)-3,6-Dibenzyl-5-hydroxypiperidin-2-one

Following the procedures outlined in Examples 2–6, and replacing L-cylohexylalanine methyl ester with L-phenylalanine methyl ester in Example 2 and methyl -3-methyl-2-oxobutyrate with methyl 3-phenyl-2-oxo-propionate in Example 4 provides the title compound.

EXAMPLE 10

(2S,4S,5S) 5-Amino-2-benzyl-6-phenyl-4-hexanolide

Following the procedure described in Example 7 and replacing the product of Example 6 with the product of Example 9 provides the title product.

EXAMPLE 11

Diethyl 2-(3-Methyl-1-butene)phosphonate

3-Methyl-2-butanone (32.4 retool, 3.47 mL) was dissolved in 25 mL of dry THF and added via cannula to a cooled (−78° C.) solution of sodium bis (trimethylsilyl) amide (1.0M solution in THF, 36 mL, 35.6 retool). The resulting solution was stirred at −78° C. for 50 minutes, added via cannula to a solution of diethyl chlorophosphonate (7.0 mL, 48.6 retool), at −78° C. The mixture was stirred at −78 ° C. for 10 minutes under N$_2$ and then allowed to warm to ambient temperature over 50 minutes. Saturated aqueous NH$_4$Cl was added and the solution was diluted with diethyl ether and the organic layer was separated. The organic solution was washed with saturated NH$_4$Cl and saturated aqueous NaHCO$_3$, dried (MgSO$_4$), and filtered. The solvent volume was reduced from 250 to 100 mL by distillation at atmospheric pressure to remove the diethyl ether and THF. The product was distilled to give 4.5 g of a clear oil (63%). b.p. 94° C. (0.15 nun Hg). $^1$H NMR (CDCl$_3$, 300 MHz) δ4.81 (dd, 1H), 4.50 (m, 1H), 4.18 (5-line multiplier, 4H), 2.42 (7-line multiplet, J=6Hz, 1H), 1.36 (m, J=6Hz, 4H), 1.11 (d, J=6Hz, 6H); MS (FAB) 223 (M+1).

EXAMPLE 12

(2-Isopropylpropen-2-yl) trimethylsilane

Trimethylsilylmethylmagnesium chloride was generated by reacting chloromethyltrimethylsilane (63 mL, 451 mmol) in 150 mL of dry THF with magnesium turnings (11 g, 453 mmol) and a catalytic amount of 1,2 dibromoethane (250 mL). After most of the magnesium had reacted, the mixture was heated to reflux for 30 minutes, cooled to ambient temperature and nickel acetylacetonate (1.93 g, 7.5 mmol, 0.05 equivalents) was added to the solution, followed by the dropwise addition of the enol phosponate prepared in Example 11 (33.4 g, 150 retool) dissolved in 150 mL of THF. The resulting black solution was stirred at ambient temperature for 1.5 hours, then cannulated into a two-phase mixture of saturated aqueous NH$_4$Cl (200 mL) and diethyl ether (200 mL). The organic layer was separated, and the green aqueous layer was extracted three times with ether. The combined organic extracts were washed with saturated aqueous NH$_4$Cl and saturated aqueous NaCl and dried over MgSO$_4$. The diethyl ether and THF were removed by distillation at atmospheric pressure (35°–70° C.). Vacuum distillation of the residue gave 18.1 g (78%) of a clear oil. b.p. 64°–69° C. (40 mm Hg). IR (CDCl$_3$) 2840–3000, 1623, 1240, 800–880 cm$^{-1}$. $^1$H NMR (CDCl$_3$, 300 MHz) δ4.60 (dd, 1 H), 4.48 (m, 1H), 2.05 (7-line multiplet, J=6Hz, 1H), 1.53 (d, 2H), 1.02 (d, J=6Hz); MS (EI) 156 (M+).

EXAMPLE 13

Alternative Preparation of (2-Isopropylpropen-2-yl)trimethylsilane

Cerium chloride heptahydrate (37 g, 100 mmol), was stirred and heated to 150° C. under vacuum (0.12 mm Hg) for 2 hours to remove water. The solid was cooled to ambient temperature and 210 mL of THF was added dropwise with stirring. The suspension was stirred at ambient temperature under N$_2$ for 2 hours, cooled to −70° C. and trimethylsilylmethylmagnesium chloride (1.0M in diethyl ether, 100 mL, 100 mmol) was added dropwise. After 5 minutes of additional stirring, ethyl isobutyrate (4.8 g, 41 mmol) was added. The reaction mixture was allowed to warm to ambient temperature overnight, cooled to 4° C. with an ice water-bath, and 140 mL of 1M HCl was added. The layers were separated, and the aqueous layer was extracted twice with diethyl ether. The combined organic extracts were washed with saturated NaHCO$_3$, dried over Na$_2$SO$_4$, filtered, and reduced to a volume of 80 mL by distillation at atmospheric pressure. The concentrated solution was mixed with 100 mL of methylene chloride and 15 g silica and stirred 2 hours at ambient temperature. The mixture was filtered and the filtrate was distilled at atmospheric pressure to remove solvents, then at 90°–125° C. (98 mm Hg) to give 2.92 g (46%) of a yellow oil which was identical to the compound prepared in Example 12.

EXAMPLE 14

Alternative Preparation of (2-Isopropylpropen-2-yl)trimethylsilane

To a solution of 2.5M n-butyllithium in hexane (10 retool) is added N, N, N', N'-tetramethylethylenediamine (TMEDA) (10 retool). The temperature of the reaction mixture rises to 40°–50° C. during addition. After stirring for 30 minutes, 2,3-dimethyl-1-butene (20 retool) is added and the reaction mixture stirred for 5 hours at ambient temperature, cooled to 0° C., and a solution of chlorotrimethylsilane (30 mmol) in hexane is added. Insoluble salts are removed by filtration after 1 hour, and the hexane filtrate is washed with saturated $NH_4Cl$ solution, dried ($MgSO_4$), and the hexane removed by atmospheric distillation. The product is obtained by vacuum distillation.

EXAMPLE 15

N-Methyl, N-Methoxy Amide of N-CBz-L-Cyclohexylalanine

A 500 mL three-neck flask equipped with a mechanical stirrer and graduated addition funnel was charged with methylene chloride (120 mL) and N,O-dimethylhydroxylamine hydrochloride (19.5 g, 200 mmol). The suspension was stirred at 0° C. and to it was added dropwise N-methylpiperidine (25.5 mL, 210 retool) maintaining the temperature at 5° C. or below during the addition. The resulting clear solution was kept at 0° C. and used in the following procedure.

A 2 L three-neck flask equipped with a mechanical stirrer and addition funnel was cooled to −20 ° C. under $N_2$. The flask was charged with N-Cbz-L-cyclohexylalanine (61.1 g, 200 retool), $CH_2Cl_2$ (900 mL) and THF (230 mL). To the stirred solution was then added N-methypiperidine (25.5 mL, 210 mmol) followed by methyl chloroformate (15.4 mL, 200 mmol). The reaction temperature was held at −15 to −20° C. during the additions. After 2 minutes, the solution of amine prepared above was added. The cooling bath was removed and the solution was warmed to ambient temperature over a period of 4 hours. The solution was then recooled to 5° C. and washed with two 250 mL portions of 0.2N HCl followed by two 250 mL portions of 0.5N NaOH and finally with 200 mL of saturated brine. The organic phase was dried over $MgSO_4$ and concentrated in vacuo at 30°–35° C. The residue was further evacuated to a constant weight and then purified by chromatography on the Waters Prep 500A eluting with (30% ethyl acetate/70% hexanes) to give 48.8 g (70% yield) of the desired amide. $[\alpha]^{23}{}_D+5.5°$. $^1$H NMR ($CDCl_3$, 300 MHz) δ0.80–1.74 (complex m, 12 H), 1.84–1.95 (m, 1H), 3.20 (s, 3H), 3.80 (s, 3H), 4.76–4.88 (m, 1H), 5.10 (q, J=11.4Hz, 2H), 5.28 (d, J=8.7z, 1H), 7.28–7.44 (complex m, 5H). MS (DCI/NH$_3$) 349 (M+H)$^+$, 366 (M+NH$_4$)$^+$. Analysis calcd for $C_{19}H_{28}N_2O_4$: C, 65.49; H, 8.10; N, 8.04. Found: C, 65.68; H, 8.09; N, 8.01.

EXAMPLE 16

N-CBz-L-Cyclohexylalanal

A 500 mL 3-neck round bottom flask equipped with a mechanical stirrer was charged under $N_2$ with 95% lithium aluminum hydride powder (1.32 g, 33 mmol) and anhydrous diethyl ether (150 mL). The suspension was stirred for 1 hour at ambient temperature and then cooled to −50° C. with a dry ice/isopropanol bath. To the suspension was added dropwise a solution of the amide resulting from Example 15 (10.5 g, 30 retool) dissolved in 20 mL of anydrous Et$_2$O. The reaction mixture was warmed to 5° C., stirred for 30 minutes and recooled to −50° C. A solution of potassium bisulfate (7.2 g, 53 mmol) dissolved in 20 mL of water was added very slowly to the reaction mixture. Gas evolution and an exotherm to −10° C. was observed. The solution was stirred at ambient temperature for 1.5 hours, filtered through a plug of Celite ®, and the Celite ® plug was washed thoroughly with Et$_2$O. The combined organics were washed 3×30 mL with cold 1N HCl, 2×30 mL with saturated NaHCO$_3$, and 1×30 mL with saturated brine. The solution was dried over $MgSO_4$ and concentrated in vacuo at 30° C. to give 8.2 g (94% yield) of the title compound as a white solid. The crude material was stored under $N_2$ at −20° C. $^1$H NMR ($CDCl_3$, 300 MHz) δ0.83–1.86 (complex 13 H), 4.30–4.42 (m, 1H), 5.12 ( s, 3H), 7.26–7.40 (m, 5H), 9.59 (s, 1H). MS (DCI/NH$_3$) 290 (M+H)$^+$, 307 (M+NH$_4$)$^+$. Analysis calcd for $C_{17}H_{23}N_1O_3$: C, 69.44; H, 8.01; N, 4.84. Found: C, 69.44; H, 8.21; N, 4.83.

EXAMPLE 17

(2S,3S) and (2S,3R) 2-Benzyloxycarbonylamino-1-cyclohexyl-3-hydroxy-5-isopropyl-5-hexene To SnCl$_4$ 1.0M in $CH_2Cl_2$ (85.0 mL, 85.0 mmol) at −78° C. under $N_2$ was added dropwise over 30 minutes a solution of the aldehyde resulting from Example 16 (16.5 g, 57.0 mmol) in 100 mL of $CH_2Cl_2$. The resulting solution was stirred at −78° C. for 2 hours and a solution of the product of Example 12, 13, or 14, 3- (2-isopropylpropen-1-yl) trimethyl silane, (10.9 g, 70.0 retool) in 50 mL of $CH_2Cl_2$ was added dropwise over 30 minutes. The reaction mixture was stirred at −78° C. for 1 hour and quenched with 100 mL of distilled water. The aqueous phase was extracted 3×50 mL with $CH_2Cl_2$. The extracts were combined, washed with 50 mL saturated brine, dried (MgSO$_4$) and concentrated in vacuo to give 19.7 g (92%) of an amber oil. TLC analysis (20% EtOAc/80% hexanes using a para-anisaldehyde stain) showed two diastereomeric alcohols R$_f$=0.34 and 0.26. The crude alcohols were purified by chromatography eluting with 20% ethyl acetate/80% hexanes to give 14.7 g (69%) of the (2S,3S) homoallylic alcohol. R$_f$=0.34. m.p. 63°–65° C. $[\alpha]^{23}{}_D=−35.0°$ (c=1.21, CHCl$_3$). $^1$H NMR (CDCl$_3$) δ0.75–1.00 (m, 1H), 1.01 (d, J=7.5Hz, 3H), 1.05 (d, J=7.5Hz, 3H), 1.07–1.91 (complex m, 13H), 2.06–2.34 (m, 3H), 3.60–3.80 (complex m, 2H), 4.79 (s, 1H), 4.89–4.94 (m, 2H), 5.12 (s, 2H), 7.25–7.40 (m, 5H). MS (DCI/NH$_3$) 374 (M+H)$^+$, 391 (M+NH$_4$)$^+$. Analysis calcd for $C_{23}H_{35}N_1O_3$: C, 73.96; H, 9.44; N, 3.75. Found: C, 73.52; H, 9.14; N, 3.64.

Chromatography also afforded the (2S,3R) diastereomer 1.4 g (7% yield). R$_f$=0.26. m.p. 74°–76° C. $[\alpha]^{23}{}_D=−43.8°$ (c=0.99, CHCl$_3$). $^1$H NMR (CDCl$_3$, 300 MHz) δ0.72–0.90 (m, 1H), 1.00 (d, J=7.5Hz, 3H), 1.04 (d, J=7.5Hz, 3H), 0.92–1.92 (complex m, 12H), 2.04–2.16 (complex m, 2H), 2.18–2.30 (m, 2H), 3.68–3.83 (m, 2H), 4.82 (s, 1H), 4.84 (d, J=9.3Hz, 1H), 4.92 (s, 1H), 5.09 (d, J=10.5Hz, 1H), 5.13 (d J=10.5Hz, 1H), 7.25–7.40 (m, 5H). MS (DCI/NH$_3$) 374 (M+H)$^+$, 391 (M+NH$_4$)$^+$. Analysis calcd. for C$_{23}$H$_{35}$NO$_3$: C, 73.96; H, 9.44; N, 3.75. Found: C,74.25; H, 9.53; N, 3.82.

EXAMPLE 18 tert-Butyldimethylsilyl Ether of (2S,3S)-2-Benzyloxycarbonylamino-1-cyclohexyl-3-hydroxy-5-isopropyl-5-hexene A solution of the (2S,3S) alcohol prepared in Example 17 (374 rag, 1.0 mmol), tert-butyldimethylsilyl chloride (226 rag, 1.5 retool) and imidazole (170 mg, 2.5 mmol) in 1 mL DMF was heated at 35° C. for 8 hours. The solution was partitioned between Et$_2$O and H$_2$O. The aqueous phase was extracted 3×15 mL with Et$_2$O. The extracts were combined, washed with saturated brine, dried (MgSO$_4$) and concentrated in vacuo to give a viscous oil. The crude product was flash chromatographed on a 12" column of silica eluting with 10% EtOAc/90% hexanes to give 460 mg (94%) of a colorless oil. [α]$^{23}_D$= −16.2° (c=1.18, CHCl$_3$). $^1$H NMR (CDCl$_3$, 300 MHz) δ0.09 (s, 6H), 0.89 (s, 9H), 0.82–1.84 (complex m, 19H), 2.04–2.29 (m, 3H), 3. 67–3.90 (m, 2H), 4.72 (s, 1H), 4.85 (s, 1H), 4.89 (bd, J=9.3Hz, 1H), 5.10 (s, 2H), 7.27–7.39 (m, 5H). MS (DCI/NH$_3$) 488 (M+H)$^+$. Analysis calcd for C$_{29}$H$_{49}$NO$_3$Si: C, 71.41; H, 10.13; N, 2.87. Found: C, 71.72; H, 10.19; N, 2.82.

EXAMPLE 19

(2S,3S,5S)-2-Benzyloxycarbonylamino-1-cyclohexyl-3,6-dihydroxy-5-isopropylhexane To (2S,4S,5S)-5-benzyloxycarbonylamino-6-cyclohexyl-2-isopropyl-4-hexanolide (J. Med. Chem. 31, 1839–46 (1988), 3.88 g, 10.0 mmol) and CaCl$_2$ (2.22 g, 20.0 retool) dissolved in a mixture of 60 mL ethanol and 60 mL THF and cooled to 0° C. was added portionwise NaBH$_4$ (1.5 g, 40.0 mmol) resulting in vigorous gas evolution and an exotherm. The resulting solution was stirred at 0° C. for 1 hour and then at ambient temperature for 1 hour, diluted with 100 mL of diethyl ether and filtered through a plug of Celite ®. The filtrate was cooled to 0° C. and quenched by the addition of 1M KHSO$_4$ until bubbling ceased. The organic phase was washed with 2×20 mL of saturated NaHCO$_3$ and 2×20 mL of saturated brine, dried (MgSO$_4$) and concentrated in vacuo to a give a white solid. Recrystallization from EtOAc/hexanes gave 3.67 g (94%) of the (2S,3S,5S)-diastereomer. m.p. 113°–114° C. [α]$^{25}_D$= −32.0° (c=1.025, CHCl$_3$). $^1$H NMR (C$_6$D$_6$, 300 MHz) δ0.76 (d, J=7.5Hz, 3H), 0.79 (d, J=7.5Hz, 3H), 0.75–1.74 (complex m, 18H), 1.98–2.09 (bd, J=11.1Hz, 1 H), 3.28–3.41 (m, 2H), 3.62–3.70 (m, 1H), 3.90–4.00 (m, 1H), 4.88 (d, J=9.6Hz, 1H), 5.12 (s, 2H), 7.00–7.30 (m, 5H). MS (DCI/NH$_3$) 392 (M+H)$^+$, 409 (M+NH$_4$)$^+$. Analysis calcd for C$_{23}$H$_{37}$NO$_4$: C, 70.55; H, 9.52; N, 3.58. Found: C, 70.78; H, 9.54; N, 3.56.

EXAMPLE 20 tert-Butyldimethylsilyl Ethers of (2S,3S,5S) and (2S, 3S, 5R) -2-Benzyloxycarbonylamino-1-cyclohexyl-3,6-dihydroxy-5-isopropylhexane To a solution of borane/dimethylsulfide (583 µL, 6.2 mmol) in 5 mL of anhydrous THF at −78° C. was added 1.0 g (2.1 mmol) of the TBDMS ether resulting from Example 18. The resulting solution was stirred at ambient temperature for 16 hours, recooled to 0° C., and aqueous 1M NaHCO$_3$ (24 mL, 24 mmol) was added followed immediately by careful addition of 30% H$_2$O$_2$ (3.4 mL). The mixture was stirred vigorously for 3 hours at ambient temperature and partitioned with Et$_2$O. The aqueous phase was extracted 3×20 mL with Et$_2$O. The combined organic extracts were washed with brine, dried (MgSO$_4$), and concentrated in vacuo. The crude product was purified by silica gel chromatography eluting with 20% EtOAc/80% hexanes to give 552 mg (52%) of the (2S,3S,5S) diastereomer, which after deprotection with tetrabutylammonium fluoride (TBAF) was identical to the diol prepared in Example 21. For the (2S,3S,5S) diastereomer: R$_f$=0.22. [α]$^{23}_D$= −21.4° (c=0.92, CHCl$_3$). $^1$H NMR (CDCl$_3$, 300 MHz) δ0.06 (s, 3H), 0.07 (s, 3H), 0.85 (d, J=7.5Hz, 3H), 0.88 (s, 9H), 0.92 (d, J=7. 5Hz, 3H), 0.80–1.85 (complex m, 18H), 3.30–3.92 (complex m, 4H), 4.84 (d, J=9.9Hz, 1H), 5.04 (d, J=12.0Hz, 1H), 5.15 (d, J=12.0Hz, 1H), 7.26–7.38 (complex m, 5H). MS (DCI/NH$_3$) 506 (M+H)$^+$, 523 (M+NH$_4$)$^+$. Analysis calcd for C$_{29}$H$_{51}$NO$_4$Si: C, 68.86; H, 10.16; N, 2.77. Found: C, 68.13; H, 9.89; N, 2.98.

Also obtained from the chromatography was the (2S,3S,5R)-diastereomer (216 rag, 20%). R$_f$=0.33. [α]$^{23}_D$ = −10.2° (c=1.56, CHCl$_3$). $^1$H NMR (CDCl$_3$, 300 MHz) δ0.08 (s, 3H), 0.09 (s, 3H), 0.78–1.90 (complex m, 18H), 0.82 (d, J=7.5Hz, 3H), 0.95 (d, J=7.5Hz, 3H), 0.88 (s, 9H), 3.52–3.63 (m, 2H), 3.78–3.88 (complex m, 2H), 3.81 (d, J=12.0Hz, 1H), 5.10 (s, 2H), 7.30–7.38 (complex, 5H). MS (DCI/NH$_3$) 506 (M+H)$^+$. Analysis calcd for C$_{29}$H$_{51}$NO$_4$Si: C, 68.86; H, 10.16; N, 2.77. Found: C, 68.34; H, 9.87; N, 2.72.

EXAMPLE 21

(2S,3S,5S) and (2S,3S,5R) -2-Benzyloxycarbonylamino-1-cyclohexyl-3,6-dihydroxy-5-isopropyl-hexane To a solution of borane/dimethylsulfide (BH$_3$·SMe$_2$, 380 µL, 4.0 retool) dissolved in 2 mL of anhydrous THF and cooled to −30° C. was added a solution of the (2S,3S) alcohol prepared in Example 17 (520 mg, 1.4 mmol) in 10 mL anhydrous THF. The reaction was stirred at ambient temperature for 4 hours and recooled to 0° C. To the reaction vessel was added carefully 3N sodium hydroxide (700 µL) followed immediately by 30% hydrogen peroxide (700 µL). The mixture was stirred vigorously for 3 hours at ambient temperature and partitioned with ether. The aqueous phase was extracted 3×20 mL with Et$_2$O. The combined organic extracts were washed with brine, dried over magnesium sulfate and concentrated to give 511 mg (93%) of a white solid. TLC analysis showed one spot which by $^1$H NMR analysis in benzene-d$_6$ showed a 1:1 mixture of diastereomers. Flash chromatography of the mixture eluting with 30% EtOAc/70% hexanes gave only partial separation of the diastereomers but afforded pure samples of each for characterization. The more polar (2S,3S,5S)-diastereomer was identical by $^1$H NMR to the diol prepared in Example 21. m.p. 112°–113° C. [α]$^{23}_D$= −32.4° (c=1.0, CHCl$_3$). Anal calcd for C$_{23}$H$_{37}$NO$_4$: C, 70.55; H, 9.52; N, 3.58. Found: C, 70.99; H, 9.40; N, 3.60.

Also obtained was the (2S,3S,5R) -diastereomer: [α]$^{25}_D$= −8.1° (c=1.70, CHCl$_3$); $^1$H NMR (C$_6$D$_6$, 300

MHz) δ0.70 (d, J=7.5Hz, 6H), 0.62-1.74 (complex m, 18H), 2.02-2.09 (bd, J=11.1Hz, 1H), 3.23 (dd, J=9.6Hz, J=9.6 Hz, 1H), 3.45 (dd, J=9.6Hz, J=3.6Hz, 1H), 3.55-3.64 (m, 1H), 3.94-4.06 (m, 1H), 5.08 (s, 2H), 5.18 (d, J=9.6 Hz 1H), 6.95-7.26 (m, 5H); MS (DCI/NH$_3$) 392 (M+H)$^+$, 409 (M+NH$_4$)$^+$; HRMS/FAB Calcd for C$_{23}$H$_{37}$NO$_4$: 392.2801. Found: 392.2813.

EXAMPLE 22

(2S,4S,5S)-5-Benzyloxycarbonylamino-6-cyclohexyl-2-isopropyl-4-hexanolide

Using the procedure of Sharpless et al. (J. Org. Chem. 46, 3936-3938 (1981)), a mixture of the (2S,3S,5S)-diol prepared in Example 19 (1.0 g, 2.56 mmol) and sodium periodate (2.24 g, 10.5 mmol) was dissolved in 8 mL carbon tetrachloride, 8 mL acetonitrile and 12 mL water. To the resulting solution was added a catalytic amount of RuCl$_3$·H$_2$O (11.6 mg, 0.056 mmol). The mixture was stirred for 6 hours at ambient temperature and diluted with 40 mL CH$_2$Cl$_2$. The organic extracts were filtered through a pad of Celite ®, washed 2×20 mL with saturated brine, dried over MgSO$_4$ and concentrated in vacuo to give the crude CBz-lactone. Purification of the lactone by silica gel chromatography (1:4 ethyl acetate:hexane) gave 520 mg (52%) of pure lactone as a white solid, m.p 167°-168° C. which was identical to that of an authentic sample of lactone (J. Med. Chem. 31, 1839-46 (1988)). [α]$^{23}_D$=-33.0° (c=1.0, CHCl$_3$). $^1$H NMR (CDCl$_3$, 300 MHz) δ0.75-0.85 (m, 1H), 0.90 (d, J=7.5Hz, 3H), 0.96 (d, J=7.5Hz, 3H), 1.20-1.85 (complex m, 12H), 2.00-2.21 (m, 3H), 2.43-2.52 (m, 1H), 3.88-3.96 (m, 1H), 4.40-4.46 (m, 1H), 4.58 (d, J=9.6Hz, 1H), 5.12 (s, 2H), 7.24-7.40 (m, 5H). Anal calcd for C$_{23}$H$_{33}$NO$_4$: C, 71.59; H, 8.58; N, 3.61. Found: C, 70.89; H, 8.52; N, 3.61.

EXAMPLE 23

Alternative Preparation Of (2S,4S,5S)-5-Benzyloxycarbonylamino-6-cyclohexyl-2-isopropyl-4-hexanolide A solution of diol prepared in Example 19 (500 mg, 1.3 mmol) and Jones Reagent 2.7M (1.9 mL, 5.2 mmol) in 10 mL acetone was stirred vigorously at 10° C. for 3 hours. The reaction mixture was filtered through a plug of Celite ® and the plug was washed repeatedly with diethyl ether. The ether layer was washed 2×5 mL with saturated brine, dried over MgSO$_4$ and concentrated in vacuo to give a white solid. The solid was flash chromatographed on silica eluting with 20% EtOAc/80% hexanes to give 286 mg (57%) of the title compound which was identical to the lactone prepared in Example 24.

EXAMPLE 24

Alternative Preparation of (2S,4S,5S) and (2R,4S,5S)-5-Benzyloxycarbonylamino-6-cyclohexyl-2-isopropyl-4-hexanolide

EXAMPLE 24A tert-Butyldimethylsilyl Ether of (2S,3S,5S) and (2S,3S,5R)-2-Benzyloxycarbonylamino-1-cyclohexyl-3-hydroxy-5-isopropylhexanoic Acid A solution of the TBDMS ether prepared in Example 19 (3.35 g, 6.6 mmol, as a mixture of diastereomers (2.4:1, 5S:5R) and sodium periodate (5.4 g, 25 mmol) in 30 mL of carbon tetrachloride, 30 mL acetonitrile and 45 mL water was vigorously stirred until all solids had dissolved. To the resulting solution was added a catalytic amount of RuCl$_3$·H$_2$O (42 mg, 0.2 mmol). The mixture was stirred for 3 hours at ambient temperature and diluted with 50 mL methylene chloride. The aqueous phase was extracted 3×40 mL with methylene chloride. The extracts were combined, filtered through a plug of Celite ® and the plug was washed repeatedly with methylene chloride. The organics were washed 2×20 mL with saturated brine, dried over MgSO$_4$ and concentrated in vacuo to give 3.1 g (90%) of the crude title compound as a purple oil.

EXAMPLE 24B (2S,4S,5S) and (2R,4S,5S)-5-Benzyloxycarbonylamino-6-cyclohexyl-2-isopropyl-4-hexanolide To the crude oxidation product resulting from Example 24A (3.1 g, 90%) dissolved in 150 mL MeOH was added 3M HCl (13.3 mL, 40 mmol). This solution was heated at reflux for 1.5 hours and allowed to cool to ambient temperature. Upon cooling, white needles crystallized from the reaction mixture and were collected by filtration to give 1.20 g (46%) which by $^1$H NMR was a 9:1; 2S:2R mixture of diastereomers. The (2S,4S,5S)-diastereomer had a $^1$H NMR identical to that described for Example 22. For the (2R,4S,5S)-diastereomer: m.p. 117°-118° C. [α]$^{23}_D$=-2° (c=1.13, CHCl$_3$). $^1$H NMR (CDCl$_3$, 300 δ0.80 (d, J=7.5Hz, 3H), 0.82-1.0 (m, 1H), 0.97 (d, J=7.5Hz, 3H), 1.0-1.89 (complex m, 13H), 2.05-2.20 (m, 2H), 2.57 (ddd, J=12.5Hz, J=9Hz, J=5 Hz, 1H), 3.89-3.99 (m, 1H), 4.32-4.39 (m, 1H), 4.67 (d, J=9.6Hz, 1H), 5.07 (d, J=12.6Hz, 1H), 5.13 (d, J=12.6Hz, 1H), 7.29-7.38 (m, 5H). MS (DCI/NH$_3$) m/e 405 (M+H+NH$_3$)$^+$.

EXAMPLE 25

Alternative Preparation of (2S,4S,5S)-5-Benzyloxycarbonylamino-6-cyclohexyl-2-isopropyl-4-hexanolide

EXAMPLE 25A tert-Butyldimethylsilyl Ether of (3S,5S,6S)-N-Cbz-6-Cyclohexylmethyl-5-hydroxy-3-isopropyl-piperidin-2-one The carboxylic acid resulting from Example 24A is dissolved in DMF, stirred at 0°-5° C. and 1.1 equivalents of dicyclohexylcarbodiimide (DCC) and dimethylaminopyridine (DMAP) are added. The bath is removed and the reaction mixture is allowed to warm to ambient temperature and kept at ambient temperature for 18 hours. Ethyl acetate and water are added, and the aqueous layer is extracted with ethyl acetate. The combined organic extracts are dried over magnesium sulfate and concentrated under reduced pressure to afford the crude title compound as a mixture of diastereomers. The mixture is stirred with 1,8-diazabicyclo[5.4.0]undec-7-ene (DBU) in acetonitrile at temperatures between 23° to 50° C. for 18 hours. Work up gives the title compound with the isopropyl group alpha.

EXAMPLE 25B (2S,4S,5S,5-Benzyloxycarbonylamino-6-cyclohexyl-2-isopropyl-4-hexanolide The lactam resulting from Example 25A is dissolved in methanol and treated with 3M HCl using the procedure described in Example 26 to afford the title compound.

EXAMPLE 26

Alternative Preparation of (2S,4S,5S)5-Benzyloxycarbonylamino-6-cyclohexyl-2-isopropyl-4-hexanolide To a solution of 3.2 equivalents of lithium diisopropylamide (LDA) in tetrahydrofuran cooled to −78° C. is added 2 equivalents of the L-prolinol amide of isovaleric acid. The reaction mixture is stirred for 30 minutes and the known epoxide N-Cbz-2-cyclohexyl-1-oxiranyl-ethylamine (see Luly et al. J. Med. Chem. 31, 532-9 (1988)) in THF is added. After stirring for 1 hour, the reaction mixture is warmed to −25° C. and kept at that temperature for 3 hours. Dilute aqueous hydrochloric acid is added and the reaction allowed to warm to ambient temperature. The crude hydroxy amide is cyclized by treatment with methanolic hydrochloric acid by the procedure described in Example 24B. The hexanolide is purified by recrystallization.

EXAMPLE 27

3-(4-Morpholinyl)propyl (2S,4S,5S)-5-(benzyloxycarbonylamino)-6-cyclohexyl-4-hydroxy-2-isopropylhexanamide The lactam resulting from Example 25A is dissolved in 10 equivalents of 3-(4-morpholinyl)propylamine and 3 equivalents of acetic acid. The solution is warmed between 25° to 50° C. for several hours, poured into water and the product is extracted with ethyl acetate. The combined organic extracts are washed, dried over magnesium sulfate and concentrated under reduced pressure. The residue obtained is stirred with excess tetrabutylammonium fluoride (TABF) in CHCl$_3$ for 18 hours and concentrated in vacuo. The residue obtained is redissolved in ethyl acetate, washed with water, dried (MgSO$_4$), and concentrated under reduced pressure to afford the title compound.

EXAMPLE 28

3-(4-Morpholinyl)propyl (2S,4S,5S)-5-(benzyloxycarbonylamino)-6-cyclohexyl-4-hydroxy-2-isopropylhexanamide A solution of lactone prepared in Example 24 (1 equivalent) and 3-(4-morpholiny)propylamine (10 equivalents) and 3 equivalents of acetic acid were heated at 50° C. for five days. Water was added and the product was extracted with ethyl acetate, dried (MgSO$_4$), and concentrated in vacuo. The amide was recrystallized from hot ethyl acetate/hexane to give the title compound as a pure diastereomer and identical ($^1$H NMR, TLC) to a sample of Example 8.

The foregoing is merely illustrative of the invention and is not intended to limit the invention to the disclosed embodiments. Variations and changes which are obvious to one skilled in the art are intended to be within the scope and nature of the invention which are defined in the appended claims.

What is claimed is:

1. The substantially isomerically pure compound of the formula:

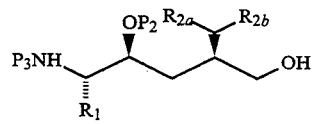

wherein P$_2$ is an O-protecting group, P$_3$ is an N-protecting group, R$_{2a}$ is hydrogen or loweralkyl, R$_{2b}$ is hydrogen, loweralkyl, cycloalkyl or phenyl and R$_1$ is cycloalkyl, cycloalkylalkyl, phenyl or benzyl.

2. A substantially isomerically pure compound of the formula:

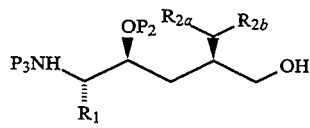

wherein P$_2$ is an O-protecting group, P$_3$ is an N-protecting group, R$_{2a}$ is hydrogen or loweralkyl, R$_{2b}$ is hydrogen, loweralkyl, cycloalkyl or phenyl and R$_1$ is cycloalkylalkyl.

3. The compound of claim 2 wherein R$_1$ is cyclohexylmethyl.

4. A compound selected from: tert-Butyldimethylsilyl Ether of (2S,3S,5S)-2-Benzyloxycarbonylamino-1-cyclohexyl-3,6dihydroxy-5-isopropylhexane and tert-Butyldimethylsilyl Ether of (2S,3S,5R)-2-Benzyloxycarbonylamino-1-cyclohexyl-3,6-dihydroxy-5-isopropylhexane.

5. A substantially isomerically pure compound of the formula:

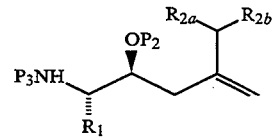

wherein P$_2$ is an O-protecting group, P$_3$ is an N-protecting group, R$_{2a}$ is hydrogen or loweralkyl, R$_{2b}$ is hydrogen, loweralkyl, cycloalkyl or phenyl and R$_1$ is cycloalkyl, cycloalkylalkyl, phenyl or benzyl.

6. A substantially isomerically pure compound of the formula:

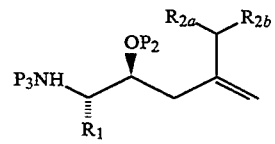

wherein P$_2$ is an O-protecting group, P$_3$ is an N-protecting group, R$_{2a}$ is hydrogen or loweralkyl, R$_{2b}$ is hydrogen, loweralkyl, cycloalkyl or phenyl and R$_1$ is cycloalkylalkyl.

7. The compound of claim 6 wherein R$_1$ is cyclohexylmethyl.

8. The compound tert-Butyldimethylsilyl Ether of (2S,3S)-2-Benzyloxycarbonylamino-1-cyclohexyl-3-hydroxy-5-isopropyl-5-hexene.

* * * * *